Figure 1:
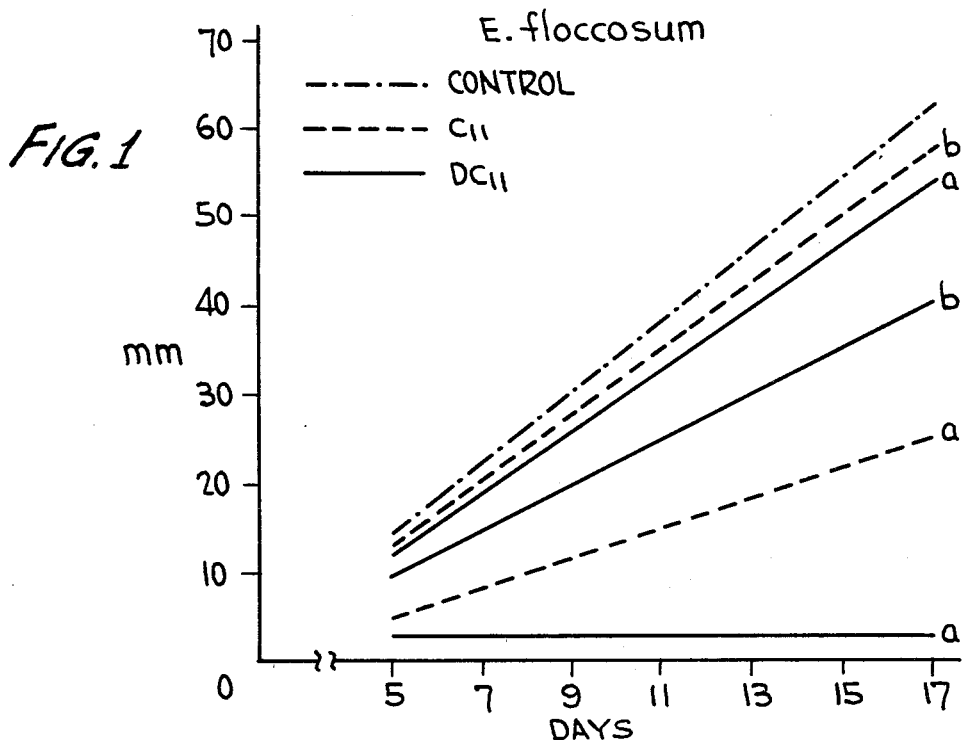

United States Patent [19]

Abrahamsson et al.

[11] Patent Number: 4,473,585
[45] Date of Patent: Sep. 25, 1984

[54] METHOD OF PROTECTING AN OBJECT AGAINST THE ATTACK OF DESTRUCTIVE FUNGI EMPLOYING PERDEUTERIATED N-HENDECANOIC ACID OR 2,2-DIDEUTERO-N-HENDECANOIC ACID

[76] Inventors: Sixten Abrahamsson, Södermalmsg. 31, 431 39 Mölndal; Dinh-Nguyen Nguyen, Lövskogsg 18, 413 20 Göteborg; Lars G. I. Hellgren, Bronsgjutareg. 13, 421 63 V.Frölunda; Jan G. Vincent, Föreningsg. 8 a, 411 27 Göteborg, all of Sweden

[21] Appl. No.: 262,820

[22] Filed: May 12, 1981

Related U.S. Application Data

[63] Continuation of Ser. No. 70,418, Aug. 28, 1979, abandoned, which is a continuation of Ser. No. 763,587, Jan. 28, 1977, abandoned.

[30] Foreign Application Priority Data

Jan. 30, 1976 [SE] Sweden ............................... 7601029

[51] Int. Cl.³ ..................... A01N 37/00; A01N 37/02; A01N 37/06; A01N 37/18
[52] U.S. Cl. .................................. 424/318; 424/311; 424/312; 424/314; 424/317; 424/320

[58] Field of Search ......................................... 424/318

[56] References Cited

U.S. PATENT DOCUMENTS 3,849,458 11/1974 Dinh-Nguyen et al. ............. 260/413
3,931,413 11/1976 Frick et al. ......................... 424/317

OTHER PUBLICATIONS

Thornton; C.A., vol. 60 (1964) 12416h.
Nguyen et al.; C.A. vol. 78 (1973) 42820h.
Popescu et al.; C.A. vol. 57 (1962) 967i.
Hurka; C.A. vol. 68 (1968) 62689u.
New Drugs (1966) p. 61.

*Primary Examiner*—Allen J. Robinson
*Attorney, Agent, or Firm*—Burns, Doane, Swecker & Mathis

[57] ABSTRACT

A carboxylic acid, its salts, esters and derivatives, in which the hydrogen atoms have been replaced, partly or entirely, by deuterium has an antimycotic effect, probably because the fungi cannot metabolize the deuteriated substance. The deuteriated substances can be used for treating living plants, seeds and wood against the attack of destructive fungi, and for curing pathogenic infections of fungi in humans and animals.

1 Claim, 10 Drawing Figures

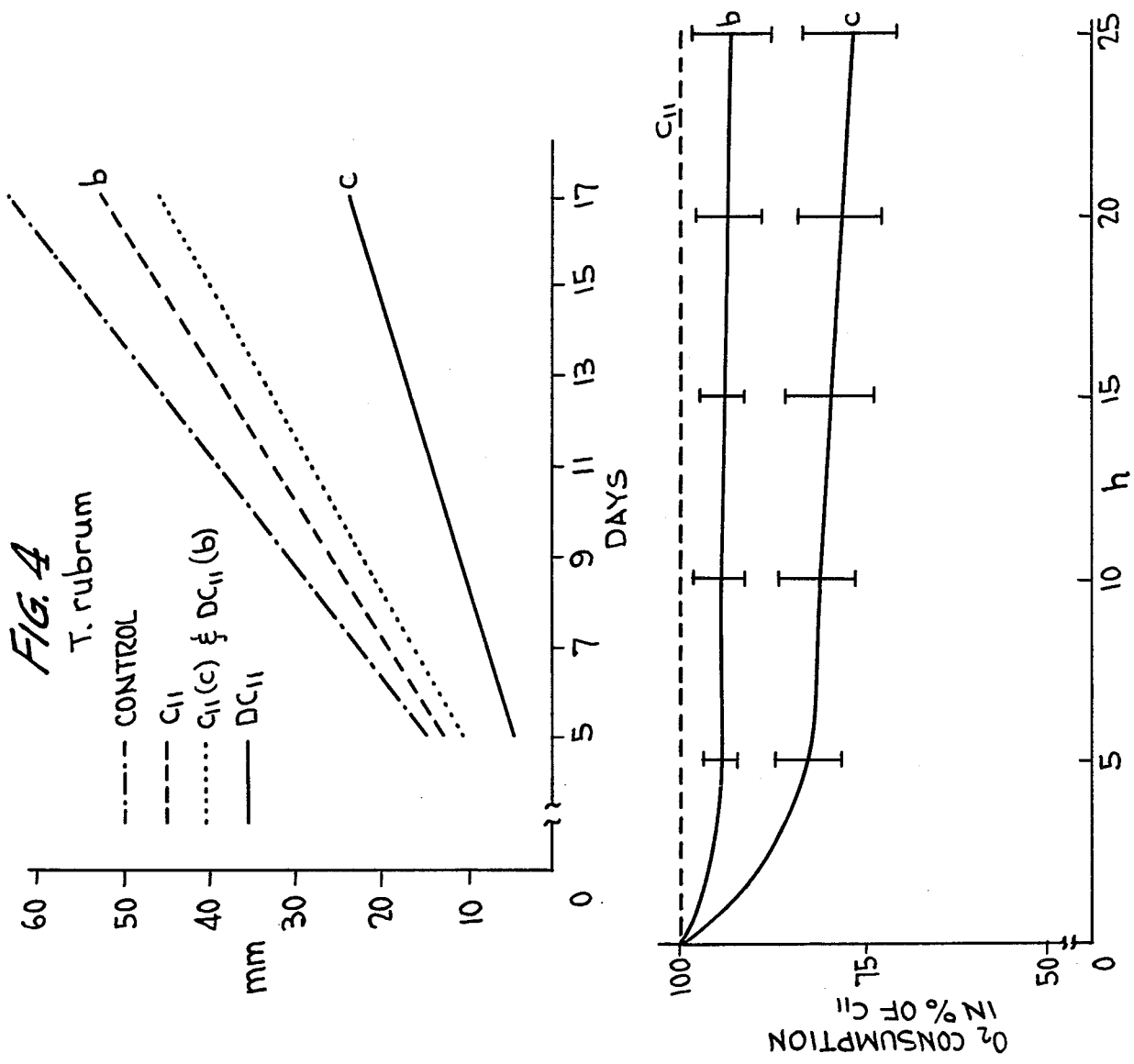
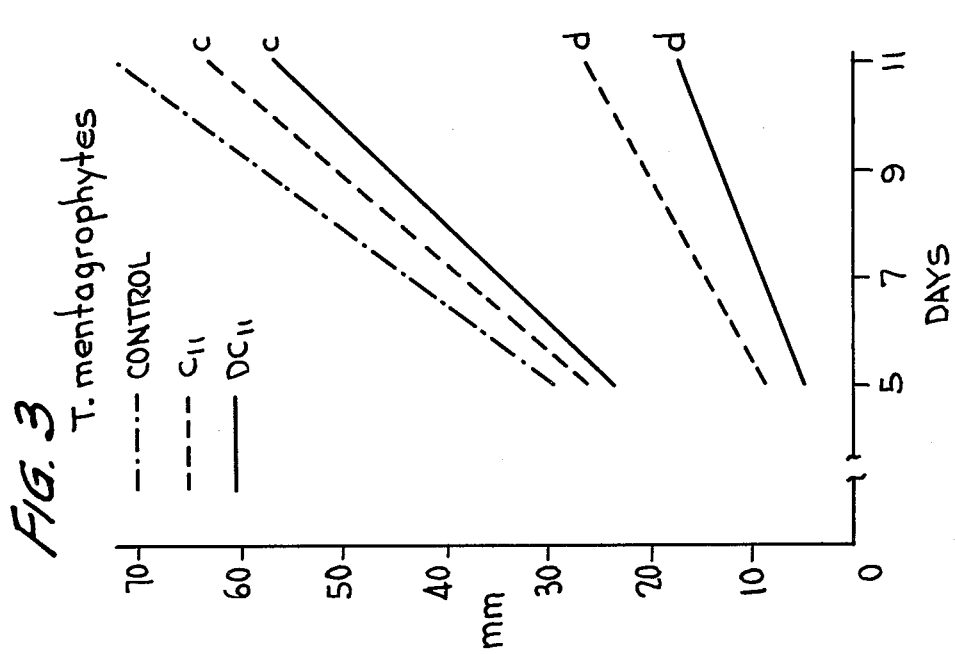

METHOD OF PROTECTING AN OBJECT AGAINST THE ATTACK OF DESTRUCTIVE FUNGI EMPLOYING PERDEUTERIATED N-HENDECANOIC ACID OR 2,2-DIDEUTERO-N-HENDECANOIC ACID

This is a continuation of application Ser. No. 70,418, filed Aug. 28, 1979 (now abandoned), which is a continuation of Ser. No. 763,587, filed Jan. 28, 1977 (now abandoned).

The present invention relates to a method of protecting biological objects such as living plants, seeds and wood against destructive fungi, especially against Fusarium (*F. colmonorum, F. oxysporum*), Fomes annosus, molds and actimomyces. This method comprises contacting the object with a composition consisting of a vehicle containing an effective amount of a compound belonging to the group comprising carboxylic acids containing up to 22 carbon atoms and their salts, esters and derivatives, in which at least two hydrogen atoms are replaced by deuterium.

The invention also relates to a method of protecting human and animal skin and mucous membranes against tinea caused by dermatophytes, especially Trichophyton, Microsporum, Epidermophyton and also towards molds (Apsergillus) and Candida. This method comprises contacting the infected area with a composition consisting of a vehicle containing an effective amount of a compound belonging to the group comprising carboxylic acids containing up to 22 carbon atoms and their salts, esters and derivatives, in which at least two hydrogen atoms are replaced by deuterium.

It is well-known that carboxylic acids have an antimycotic effect. This effect decreases with a rising number of atoms in their carbon chain. It seems to be dependent on the acid milieu, caused by the dissociation of the acid. However, the antimycotic effect of deuteriated carboxylic acids seems in a very little degree to be dependent on the degree of acidity. It seems more to be dependent on the fact that the fungi use the carboxylic acids as a carbon source. The binding energy between deuterium and carbon is much stronger than between hydrogen (protium) and carbon which results in the fact that the fungi or their enzymatic systems cannot break the bond between deuterium and carbon, i.e. cannot metabolize the deuteraited substances. This can result in inhibition of the fungal growth. The principle seems to be generally applicable on all carboxylic acids and their derivatives assimilated by the fungi.

Also if a very small part of the carboxylic acid is deuteriated, it has a certain antimycotic effect.

We have found that at least two hydrogen atoms in the carboxylic acid molecule shall be replaced by deuterium. It is desired that at least 90% of all carboxylic acid molecules consist of such deuteriated molecules. Mostly we have used carboxylic acids which are perdeuteriated, i.e. more than 99 percent of the hydrogen atoms are replaced by deuterium. Also in this case it is desired that at least 90% of all carboxylic acid molecules consist of such perdeuteriated molecules. The deuteriating procedure is not considered in the invention and it can be performed in well-known ways. A perdeuteriation can be performed using a method described in the Swedish Pat. No. 358,875.

From the deuteriated carboxylic acids there can be used those with a straight chain and containing 2–22 carbon atoms. Carboxylic acids having short carbon chains may produce undesired effects on humans and animals. Therefore, when treating infections in humans and animals we prefer carboxylic acids containing 10–18 carbon atoms. Especially suitable is n-hendecanoic acid with 11 carbon atoms.

The deuteriated carboxylic acid can be used as such or as a derivative, such as an amide or amine, an ester or a salt. If the carboxylic acid does not possess the desired physical characteristics, for example a desired degree of water-solubility, it may be transformed into a derivative possessing such desired characteristics. In treatment of materials which are to be placed in contact with water or are to be exposed to weather and wind, the application of deuterated carboxylic acids with a relatively low water-solubility is preferred.

When using a water-insoluble deuteriated carboxylic acid or its derivative, the acid can be dissolved in an organic solvent, and in this form applied on the biological material which shall be treated. We propose, however, to use the acid and its derivatives as a dispersion in water, preferably in a concentration below 2 percent by volume. Such a dispersion can be manufactured in a well-known manner. By adding a small amount of a surfactant it is possible to achieve a stable dispersion.

EXAMPLES

Perdeuteriated n-hendecanoic acid (normal) was synthezised according to the method described in the Swedish Pat. No. 358 875. The deuteriated acid was dispersed in water in a concentration of 50 mg/l. The dispersion was stable enough for practical use. With this dispersion plants were treated which before had been infected with *Fusarium culmonorum* and *Fusarium oxysporum*. A considerable inhibiting effect was achieved on the growth of the fungi. The increase of the antifungal effect was about 10 percent when compared with the effect of the non-deuteriated analogue in 24 replicates.

Table

Percent of inhibition of n-hendecanoic acid respectively deuteriated n-hendecanoic acid expressed as percentage of non-treated controls.

| Type of fungus | $C_{11}$ | $DC_{11}$ | No treatment |
|---|---|---|---|
| *Fusarium culmonorum* | 32.1% | 51.0% | 0% |
| *Fusarium oxysporum* | 5.3% | 12.3% | 0% |

Fungi were in the same way exposed to a partially deuteriated carboxyl acid (2,2-dideuterio-n-hendecanoic acid) in concentrations of 50 mg/l. In 6 replicates a significant inhibiting effect was observed on the fungal growth, which was at least 10 percent superior to the non-deuteriated analogue. The results were comparable with those achieved with the perdeuteriated n-hendecanoic acid.

The inhibiting effect of the perdeuteriated hendecanamide was in the same way compared with that of the non-deuteriated analogue. Also in this case an increase of the antifungal effect was achieved. The result was about 10 percent better than that of the non-deuteriated analogue.

Thus is has been possible to clearly show that perdeuteriated and partially deuteriated n-hendecanoic acid and its derivatives are superior to non-deuteriated analogues regarding their antimycotic effect.

An increase of the antimycotic effect of a fatty acid or its derivatives by deuteration means, in relationship with the present standpoint of science, a new important chemotherapeutical principle. Deuteration of such substances creates a possibility to reduce the concentration of an antimycotic substance considerably while still reaching the desired antimycotic effect.

The principle for use of deuterated fatty acids and their derivatives against pathogenic fungi causing disease in humans and animals is the same as described above. It has been shown that perdeuteriated or partially deuteriated fatty acids and their derivatives, particularly the amide and amine derivatives, can be added to suitable vehicles for the treatment of fungal infections in man and animals. According to the invention the deuteriated or partially deuteriated acids and their derivatives are effective in a concentration of about 50-100 $\mu$g/ml in vehicles of the type commonly used to remedy skin diseases. We prefer to use a concentration of at least 5 g/l. Useful vehicles are the following: ointments (paraffin-hydrocarbons, especially vaseline, ol.-paraffini, silicone oil), creams (emulsions of hydrocarbons), polyethylene glycols (carbowaxes), liniments (based on hydrocarbons), solutions, varnishes, sprays, powders, pastes, sticks, bathoils, bath solutions, medicated plasters, rollers, oils, crystalline lipids. For mucous membranes are used: oral bases—mucilago carboxylmethylcellulose vagitories and suppositories for vagina and rectum respectively. Examples of useful pharmacological compositions:

EXAMPLE 1

70 percent ethyl alcohol 100 grams
Perdeuteriated n-hendecanoic acid 1 gram
This solution was shown to be effective towards nail infections with fungi.

EXAMPLE 2

Cremor vaselini 100 grams
Perdeuteriated n-hendecanoic acid 1 gram
This cream can be used towards fungal infections in intertriginous skin areas such as groins, anal region, interdigital regions, axillae.

Vaselinum album 100 grams
Perdeuteriated n-hendecanoic acid 1 gram
This ointment could be used towards fungal infections on extremities, trunc and head, i.e. palmar-plantar areas etc.

Talcum 100 grams
Perdeuteriated n-hendecanoic acid 1 gram
This powder is effective in intertriginous areas.

A brief account will now be given on the results of experiments in vitro and in vivo. In vitro experiments revealed that the anthrophilic fungus *Epidermophyton floccosum* was totally inhibited in its growth when the fungus was exposed to 50 $\mu$g/ml of the perdeuteriated n-hendecanoic acid, compared with a 70 percent inhibition when the non-deuteriated n-hendecanoic acid of the same concentration was used. When exposed to 25 $\mu$g/ml the inhibition was 30 percent for the perdeuteriated and about 10 percent for the non-deuteriated analogue. At exposure to 0 $\mu$g/ml the perdeuteriated n-hendecanoic acid gave rise to 10 percent inhibition compared with no inhibition for the non-deuteriated analogue.

The perdeuteriated fatty acids of the longer chain-type, such as $C_{12}$-$C_{18}$ show an indicative enhanced antifungal effect on *Epidermophyton floccosum*.

*Epidermophyton floccosum* reduced significantly the oxygen consumption when exposed to perdeuteriated n-hendecanoic acid in the concentration of 26 $\mu$g/ml and 50 $\mu$g/ml compared with exposure to its unlabelled analogue.

*Trichophyton rubrum*, when exposed to 50 $\mu$g/ml of perdeuteriated n-hendecanoic acid inhibited about 70 percent of its growth, compared with an inhibition of about 30 percent when exposed to the non-deuteriated analogue. For 25 $\mu$g/ml the inhibition was about 20 percent, for the perdeuteriated n-hendecanoic acid—compared with no inhibition at all for the non-deuteriated analogue. The results were statistically significant.

Deuteriated $C_{12}$ shows significant enhanced antifungal effect on *T. rubrum* when compared with its unlabelled analogue.

*Microsporum canis* showed a complete inhibition when exposed to 100 $\mu$g/ml of perdeuteriated n-hendecanoic acid and 70 percent inhibition when exposed to non-deuteriated analogues. Deuteriated $C_{12}$ had an indicative enhanced antifungal effect on *Microsporum canis* as compared with its unlabelled analogue.

*Epidermophyton floccosum* showed perforations and an undulating growth of its hyphes when exposed to perdeuteriated n-hendecanoic acid at concentration of 10 $\mu$g/ml, but no such effects were observed when exposed to the non-deuteriated analogue. This indicates a more potent antifungal effect of the perdeuteriated fatty acid than of the non-deuteriated analogue.

Partially deuteriated n-hendecanoic acid (2,2-dideuterio-n-hendecanoic acid) in the concentration of 50 $\mu$g/ml in 7 replicates gave approximately the same inhibiting effect on its growth as for the perdeuteriated acid on all dermatophytes tested.

The inhibiting effect of perdeuteriated hendecanoicamide compared with the effect of the non-deuteriated analogue showed a potentiation of the antimycotic effect amounting 10–25 percent in 7 replicates.

In vivo experiments with Guinea pigs revealed that 2 percent perdeuteriated n-hendecanoic acid was significantly more effective than 0.5 percent gentiana violet solution (a very potent antimycotic substance in this concentration) in healing alopecia of the Guinea pig caused by *Microsporum canis*.

Perdeuteriated n-hendecanoic acid had a statistically significant antimycotic effect on the healing of alopecia caused by *Microsporum canis* in concentrations of 1 and 2 percent of the perdeuteriated n-hendecanoic acid when compared with the non-deuteriated analogue.

Comparisons were performed between perdeuteriated fatty acids $C_{12}$-$C_{18}$ and their non-deuteriated analogues. Indicative (but not significant) differences were achieved in these series in 1 and 2 percent concentrations for the lower chained fatty acids.

The enhanced antifungal effect of some of the perdeuteriated fatty acids was still statistically significant when dimethyl-sulphoxide, respectively hydrocortisone phosphate were added.

Experiments have also been made using caesium salts of $C_{18}$ and in these experiments some increased effect of potency of perdeuteriation was observed; however not statistically significant.

Figure 6:
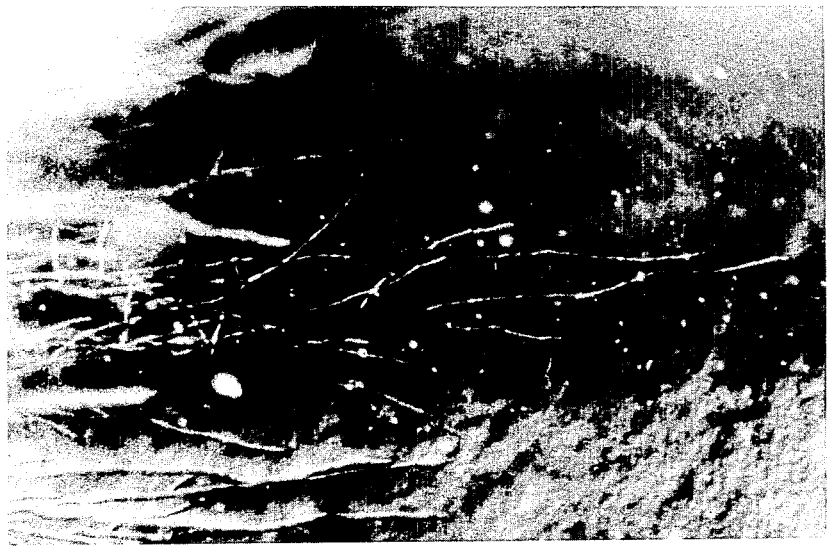
Figure 7:
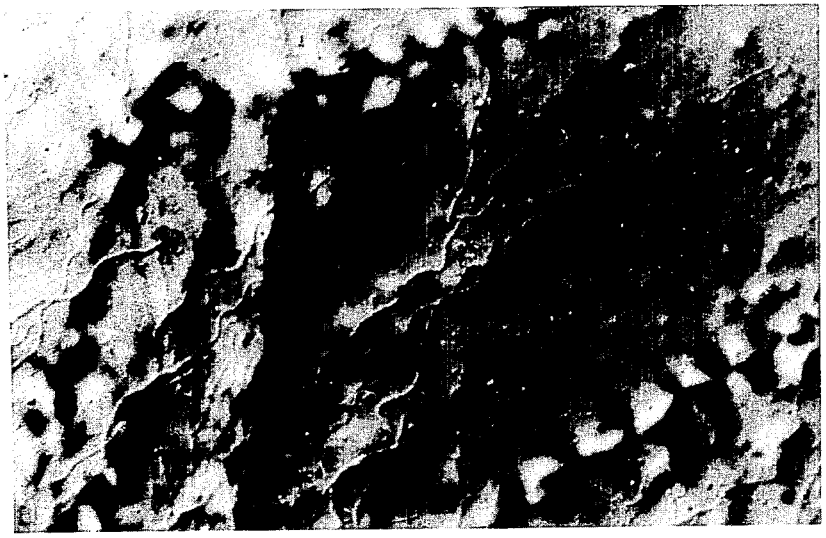
Figure 8:
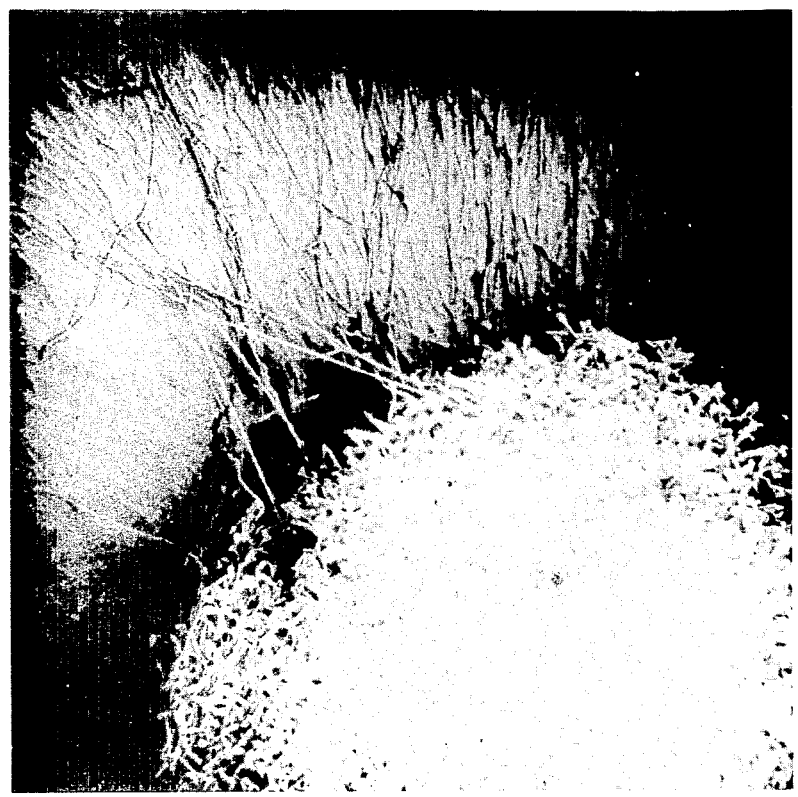
Figure 9:
Figure 10:

The invention will now be described more completely with reference to experiments. We shall first describe experiments in vitro, subsequently give an account of a morphological examination, subsequently describe experiments in vivo on Guinea pigs, and finally give an account on the useful effect of the invention on humans. The experiments are illustrated by means of FIGS. 1-10. FIGS. 1-4 illustrate the enhanced fungistatic effect of perdeuterated n-hendecanoic acid on *Epidermophyton floccosum,* FIG. 1, on *Microsporum canis,* FIG. 2, on *Trichophyton mentagrophytes,* FIG. 3, and on *Trichophyton rubrum,* FIG. 4. FIG. 5 illustrates the oxygen consumption of *Epidormophyton floccosum.* FIG. 6 is an interference contrast microscopial picture of *Epidermophyton floccosum* exposed to n-hendecanoic acid. FIG. 7 is a similar picture of *E. floccosum* exposed to perdeuteriated n-hendecanoic acid. FIG. 8 is a scanning electron microscopic picture of the mycelia of *E. floccosum* exposed to n-hendecanoic acid. FIG. 9 is a similar picture of *E. floccosum* exposed to perdeuteriated n-hendecanoic acid. FIG. 10 shows an apical segment of *E. floccosum* exposed to perdeuterated n-hendecanoic acid.

Heavy water (deuterium oxide, $D_2O$), the simplest deuterium containing compound, differs from ordinary water (protium oxide, $H_2O$) in many physical properties. In the same way molecular configuration, ionic equilibrium and vapour pressure of deuteriated substances are different from those possessing protium (hydrogen). Furthermore reaction rates for the rupture of bonds C—D, N—D and O—D are not the same as for those involving C—H, N—H and O—H. Therefore, very soon after the discovery of deuterium, in 1932 Urey and Lewis suggested that these differences in properties might give rise to differences in the chemical and biological activities of deuteriated compounds. Since then, a large number of miscellaneous investigations covering the physical, chemical and biological properties of deuteriated compounds have appeared in the literature.

Early investigations and many subsequent studies have concluded that substantial replacement of protium by deuterium is incompatible with life. While this is true for higher plants and animals which tolerate a maximum of about 35% $D_2O$, it is not valid for e.g. algae, bacteria or fungi. Chroney et al. were the first to report successful growth of the green algae *Chlorella vulgaria* and *Scenedesmus obliques* in media containing 99.7% $D_2O$ with $CO_2$ as the only carbon source. However, adaption of algae to growth in so high a concentration of deuterium oxide is a complex phenomenon illustrated by the occurence of giant cells. Among a large number of microorganisms, even fungi have been studied in order to establish how their growth and morphology are affected by replacement of $H_2O$ by $D_2O$ in culture media.

The effect of unlabelled fatty acids on fungi is well known. As long ago as 1899 Clark reported how fatty acids affected mould germination. Also early systematic studies have revealed the importance of chain length in determining the activity of fatty acids. Fatty acids were introduced as therapeutic agents for mycotic infections by Peck et al. These authors showed that human perspiration was protective against infections in general and dermatophytes in particular. They were able to demonstrate, that sweat was fungistatic due to its content of middle chain fatty acids ($C_{10}$–$C_{12}$). Since then many investigations have confirmed the therapeutic value of some fatty acids in dermatophytosis. However, the therapeutical value of the middle-chain acids, especially n-hendecen-10-oic (undecylenic) acid, is limited.

Specific, partially and fully deuterated organic compounds have been synthesised to be used in the experiments to be described below. The invention, however, is not concerned with such syntheses. Therefore, they are only described briefly. The fully deuteriated compounds will be referred to as perdeuteriated compounds.

The dermatophytes used in the in vitro experiments were monsporically selected strains of *Epidermophyton floccosum* (Harz) Langeron & Milochevitsch (1930), *Microsporum canis* Bodin (1902), *Trichophyton mentagrophytes* (Robin) Blanchard (1896) and *Trichophyton rubum* (Castellani) Sabouraud (1911). All strains originated from the collection of the Mycological Laboratory, Department of Dermatology, Sahlgren's Hospital in Göteborg. Stock cultures were maintained on Saboraud dextrose agar (Difco) slants and subcultured at monthly intervals.

The antifungal properties of unlabelled normal chain hendecanoic, dodecanoic and tetradecanoic acids (p.a., Fluka) and caesium hexadecanoate and octadecanoate were compared with their perdeuteriated analogues. Concentrations utilized were 100, 50, 25, 10, 5 and 1 μg/ml. The test substances were dispersed in the nutrient media by Ultra-Turrax (IKA) homogenisator.

The perdeuteriated normal chain hendecanoic, dodecanoic, tetradecanoic, hexadecanoic and octadecanoic acids were synthesised, according to known methods by protium-deuterium ($H_2$—$D_2$) exchange reaction occurring between the non-deuteriated sodium carboxylates ($C_{11}$, $C_{12}$, $C_{14}$, $C_{16}$, $C_{18}$) and deuterium oxide ($D_2O$) in the presence of deuterium-reduced Adams catalyst (Pt—$D_2$), sodium deuterioxide (NaOD) and deuterium peroxide ($D_2O_2$). The reaction was conducted at high temperatures. These were 225° C. for incubation of sodium hendecanoate and dodecanoate, 235° C. for that of sodium tetradecanoate, and 240° C. for that of sodium hexadecanoate and octadecanoate.

The incubations were carried out in two types of reactors. The first consisted of 20-ml sealed, long narrow-necked and round-bottomed Pyrex glass tubes; an electric furnace-and-shaker constructed by Kirsten & Stenhagen was used to accomplish the conditions needed for the exchange reaction. The second one was a 300-ml magnetically stirred reactor, made in nickel and equipped with a jacket type heater, purchased from Autoclave Engineers Inc.

Preparation of the heterogeneous catalyst (Pt—$D_2$), homogeneous catalyst (NaOD), promotor ($D_2O_2$) and sodium carboxylates, and methods of carrying out the exchange reaction were executed according to known methods. All of these are summarized by Table 1 and the following scheme:

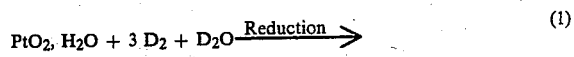

(1)

(2)

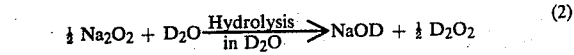

(3)

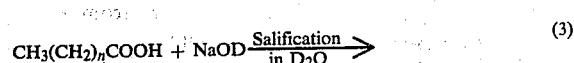

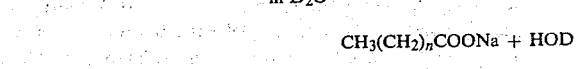

(4)

-continued $$CD_3(OD_2)_nCOONa + CD_3(CD_2)_{n-1}CD_3$$

TABLE 1

Summary of protium-deuterium exchanges

| Starting carboxylic acids | mg | mmole | PtO$_2$, H$_2$O mg | Na$_2$O$_2$ mg | D$_2$O ml | Temp. °C. | Time h | Final carboxylic acids$^a$ | mg |
|---|---|---|---|---|---|---|---|---|---|
| CH$_3$(CH$_2$)$_9$COOH$^b$ | 10000 | 53.6 | 2000 | 1870 | 140 | 225 | 24 | | |
| | | | 500$^d$ | 0 | 120$^d$ | 225$^e$ | 12$^f$ | CD$_3$(CD$_2$)$_9$COOH | 5600 |
| CH$_3$(CH$_2$)$_{10}$COOH$^b$ | 12000 | 59.9 | 3000 | 2300 | 170 | 225 | 24 | | |
| | | | 500$^d$ | 0 | 140$^d$ | 225$^e$ | 12$^f$ | CD$_3$(CD$_2$)$_{10}$COOH | 7100 |
| CH$_3$(CH$_2$)$_{12}$COOH$^c$ | 115 | 0.5 | 29 | 21.5 | 2 | 235 | 24 | | |
| | 115 | 0.5 | 29 | 21.5 | 2 | 235 | 24 | CD$_3$(CD$_2$)$_{12}$COOH | 135 |
| CH$_3$(CH$_2$)$_{14}$COOH$^b$ | 10000 | 38.9 | 2500 | 1670 | 170 | 240 | 24 | | |
| | | | 500$^d$ | 0 | 140$^d$ | 240$^e$ | 12$^f$ | CD$_3$(CD$_2$)$_{14}$COOH | 7400 |
| CH$_3$(CH$_2$)$_{16}$COOH$^b$ | 8000 | 28.1 | 2000 | 1200 | 170 | 240 | 24 | | |
| | | | 500$^d$ | 0 | 140$^d$ | 240$^e$ | 20$^f$ | CD$_3$(CD$_2$)$_{16}$COOH | 7140 |

$^a$The important by-products, the deuteriocarbons (see the reaction 4), are to communicated in another paper.
$^b$Incubation performed with nickel reactor.
$^c$Incubation performed with two separate sealed Pyrex glass tubes.
$^{d,e,f}$Amount of substances, temperature and time utilized for the second incubation.

Isolation of the principal final products was performed in the following way:

After the last incubation and after removal of water (D$_2$O and HOD) in vacuo the residue—composed of platinum catalyst, sodium deuterioxide, deuteriated sodium carboxylate, deuteriocarbon and other organic by-products—was treated with light petroleum (b.p. 40°-50°), in order to extract the deuteriocarbon. The rest of the residue was then acidified with dilute HCl at about 40° C. The organic phase was extracted with diethyl ether, washed with distilled water, and dried over Na$_2$SO$_4$ in the presence of decolourising charcoal. After removal of the solvent in vacuo, the residue obtained was either fractionally distilled under reduced pressure (in the case of C$_{11}$ acid) or crystallized from acetone (in the case of the other homologues). The perdeuteriated dodecanoic, tetradecanoic, hexadecanoic and octadecanoic acids were isolated as colourless plates melting at 40°, 50°, 59° and 65° C., respectively. The perdeuterio-hendecanoic acid obtained, as a colourless crystalline mass at room temperature, had a b.p.$_{40}$ 188° C.

These carboxylic acids, in small amount (about 10 mg), were converted into methyl esters, in absolute methanol catalysed by HCl gas, preparatory to mass spectrometric analysis. The deuterium content calculated in percent of each substance was deduced from the height of molecule-ion peaks, with correction due to the natural abundance (1.1%) of carbon-13. All these methyl perdeuterio-carboxylates had a deuterium content of more than 98 percent.

Perdeuteriated caesium hexadecanoate and octadecanoate, were prepared by reaction of stoichiometric amounts of CsOH with the corresponding acids in methanol. Both carboxylates recrystallized from acetone were isolated as colourless plates.

Standard mycelial suspensions prepared from ten day old cultures were used in all experiments.

Dilution tests were made in this way. Dispersions of the test substances in artificial, chemically well defined media were prepared. 10 ml of such substrate was poured into each tube in order to obtain seven replicas of each concentration. Each tube was then innoculated with 0.05 ml of the mycelial suspension. After one month of cultivation the mycelia were killed by addition of HgCl$_2$ and harvested by filtration under reduced pressure. The mycelial samples were carefully dried and the resulting dry weights applied for growth comparisons. Parallel experiments were performed on the solid media (Sabouraud dextrose agar, Difco). The test substances dispersed in the nutrient media were poured into Petri dishes (thickness of the substrate layer approx. 0.5 cm) innoculated exactly in the centre of the plate and incubated during three weeks. Diameters of the colonies (fifteen replicas of each concentration) were measured each 48 h and expressed in mm.

Respiratory determinations were made in this way. A conventional manometric technique was applied to measure the oxygen consumption of the fungal suspensions exposed to test substances. Warburg apparatus (Braun, Meltsungen) equipped with 14 manometers was utilized. Each vessel contained 2.3 ml of substrate (Sabouraud dextrose broth, Difco) with the dispersed test substance and 0.5 ml of the standard mycelial suspension. To assure complete absorption of CO$_2$, each vessel contained also 0.2 ml of 20% KOH solution in the centre wall. Working temperature was 30° C., and the running time 24 h. The values reported are an average of at least seven separate determination and expressed as a percentage of the non-deuterated aralogues (=100%). To assure the reproducibility of the measurements, each experiment included one non-treated control sample as an internal standard.

Differences in dermatophyte growth were tested using a desk computer by Student's t-test, level of significance 95 percent, double-sided interval. Inhibition (i) of the fungal growth was calculated according to the formula:

$$i = \frac{\bar{x}_s \times 100}{\bar{x}_c} - 100;$$

where $\bar{x}_s$ represents the arithmetical mean of fungal colonies (mm of diameter) exposed to the test substance; $\bar{x}_c$ represents the arithmetical mean of the non treated fungal colonies (mm of diameter) as control.

The results of the dilution tests are summarized in Tab. 2–10 and illustrated in FIGS. 1–4.

With a decreasing chain length the antifungal activity of the fatty acids increases and reaches a maximum at C$_{11}$. Thus the predetermined fatty acids of the longer chain type such as C$_{14}$–C$_{18}$ show a slightly (indicative) enhanced antifungal effect only on E. floccosum; the perdeuteriated dodecanoic acid (C$_{12}$) shows a significant enhanced antifungal effect on E. floccosum and T.

rubrum and an indicative effect on M. canis, when compared with their respective unlabelled analogues. This is illustrated by Table 2, which relates to dermatophytes grown on a solid substrate (Sabouraud dextrose) agar, Difco) with or without addition of perdeuteriated fatty acids ($C_{12}$-$C_{18}$) and their unlabelled analogues after eleven days of growth. The values reported are diameters (mm) of fungal colonies. These represent arithmetical means and standard deviations of seven separate determinations. Abreviations: EF: E. floccosum, MC: M. canis, TM: T. mentagrophytes, TR: T. rubrum, S: significant ($p \leq 0.05$); I: indicative ($0.05 \leq p \leq 0.10$), O: not significant.

TABLE 2

| fungus | $C_{12}$ | | $DC_{12}$ | | | $C_{14}$ | | $DC_{14}$ | | | $C_{16}$ | | $DC_{16}$ | | | $C_{18}$ | | $DC_{18}$ | | |
|---|---|---|---|---|---|---|---|---|---|---|---|---|---|---|---|---|---|---|---|---|
| | $\bar{x}$ | SD | $\bar{x}$ | SD | t-test | $\bar{x}$ | SD | $\bar{x}$ | SD | t-test | $\bar{x}$ | SD | $\bar{x}$ | SD | t-test | $\bar{x}$ | SD | $\bar{x}$ | SD | t-test |
| EF | 36.9 | 2.41 | 32.7 | 2.14 | S | 38.0 | 1.70 | 36.7 | 2.09 | I | 40.1 | 2.37 | 38.5 | 2.22 | I | 41.3 | 2.33 | 39.9 | 1.98 | I |
| MC | 55.7 | 2.50 | 53.9 | 2.37 | I | 59.2 | 2.84 | 58.7 | 3.36 | O | 62.0 | 3.24 | 61.4 | 3.70 | O | 62.8 | 3.49 | 63.2 | 3.15 | O |
| TM | 69.3 | 2.62 | 68.1 | 3.08 | O | 71.5 | 3.51 | 69.8 | 3.28 | O | 73.6 | 3.42 | 74.2 | 3.17 | O | 75.9 | 3.61 | 74.1 | 4.10 | O |
| TR | 38.0 | 2.11 | 35.2 | 1.74 | S | 39.8 | 2.05 | 38.5 | 2.43 | O | 41.4 | 2.31 | 40.1 | 1.83 | O | 41.5 | 2.74 | 40.7 | 2.56 | O |

However, all determatophytes tested showed a statistically significant growth retardation effect when exposed to the perdeuteriated n-hendecanoic acid when compared with the unlabelled analogue. The dermatophytes can be ranked according to their sensitivity in the order indicated below.

The most sensitive was demonstrated to be E. floccosum in which the inhibition was complete when exposed to 50 μg/ml of the perdeuteriated n-hendecanoic acid compared to about 70 percent of the unlabelled analogue; when exposed to 25 μg/ml the inhibition was about 30 percent for the perdeuteriated n-hendecanoic acid and about 10 percent for the unlabelled analogue. When exposed to 10 μg/ml of the perdeuteriated n-hendecanoic acid the inhibition was about 10 percent compared to any inhibition for the unlabelled analogue (Tab. 3–4, FIG. 1).

Table 3 relates to E. floccosum grown on artificial liquid substrate with or without (non-treated control) addition of perdeuteriated n-hendecanoic acid and the unlabelled analogue. The values reported are mycelial yields (mg/dry weight) after one month period of growth. These represent arithmetical means and standard deviations of seven separate determinations.

TABLE 3

| concentration | fatty acids | | | | |
|---|---|---|---|---|---|
| | $C_{11}$ | | $DC_{11}$ | | |
| (μg/ml) | $\bar{x}$ | SD | $\bar{x}$ | SD | t-test |
| 100 | 0 | 0 | 0 | 0 | |
| 50 | 16 | 2.45 | 0 | 0 | significant |
| 25 | 39 | 4.09 | 31 | 4.14 | significant |
| 10 | 45 | 4.67 | 40 | 4.88 | indicative |
| 5 | 47 | 5.08 | 43 | 5.49 | not significant |
| 1 | 44 | 5.92 | 46 | 6.21 | not significant |
| non treated control: $\bar{x} = 44 \pm 5.56$ | | | | | |

Table 4 relates to E. floccosum grown on solid substrate (Sabouraud dextrose agar, Difco) with or without (non-treated control) addition of perdeuteriated n-hendecanoic acid and the unlabelled analogue. The values reported are diameters (mm) of fungal colonies. These represent arithmetical means and standard deviations of fifteen separate determinations.

TABLE 4

| age (days) | concentration (μg/ml) | fatty acids | | | | |
|---|---|---|---|---|---|---|
| | | $C_{11}$ | | $DC_{11}$ | | |
| | | $\bar{x}$ | SD | $\bar{x}$ | SD | t-test |
| 5 | 100 | 0 | 0 | 0 | 0 | |
| | 50 | 5.0 | 1.24 | 0 | 0 | significant |
| | 25 | 13.3 | 2.50 | 9.7 | 1.81 | significant |
| | 10 | 15.2 | 1.98 | 14.0 | 2.04 | not significant |
| | non treated control: $\bar{x} = 15.1 \cdot 0.83$ | | | | | |
| 7 | 100 | 0 | 0 | 0 | 0 | |
| | 50 | 7.1 | 2.03 | 0 | 0 | significant |
| | 25 | 19.5 | 2.07 | 14.0 | 2.15 | significant |
| | 10 | 20.4 | 1.92 | 19.1 | 1.83 | indicative |
| | non treated control: $\bar{x} = 21.3 \cdot 1.79$ | | | | | |
| 9 | 100 | 0 | 0 | 0 | 0 | |
| | 50 | 10.0 | 2.52 | 0 | 0 | significant |
| | 25 | 26.1 | 2.89 | 18.4 | 2.67 | significant |
| | 10 | 27.8 | 1.83 | 26.2 | 2.72 | indicative |
| | non treated control: $\bar{x} = 28.2 \cdot 2.04$ | | | | | |
| 11 | 100 | 0 | 0 | 0 | 0 | |
| | 50 | 15.2 | 1.12 | 0 | 0 | significant |
| | 25 | 36.7 | 2.87 | 25.0 | 2.19 | significant |
| | 10 | 42.8 | 1.75 | 41.6 | 2.00 | indicative |
| | non treated control: $\bar{x} = 40.3 \cdot 2.49$ | | | | | |
| 13 | 100 | 0 | 0 | 0 | 0 | |
| | 25 | 17.0 | 1.71 | 0 | 0 | significant |
| | 25 | 42.4 | 3.04 | 30.6 | 2.82 | significant |
| | 10 | 46.0 | 2.21 | 44.5 | 2.14 | indicative |
| | non treated control: $\bar{x} = 47.3 \pm 2.33$ | | | | | |
| 15 | 100 | 0 | 0 | 0 | 0 | |
| | 50 | 21.3 | 3.24 | 0 | 0 | significant |
| | 25 | 48.1 | 2.89 | 34.3 | 3.31 | significant |
| | 10 | 57.2 | 2.92 | 52.9 | 3.08 | significant |
| | non treated control: $\bar{x} = 54.7 \pm 2.80$ | | | | | |
| 17 | 100 | 0 | 0 | 0 | 0 | |
| | 50 | 25.5 | 2.40 | 0 | 0 | significant |
| | 25 | 55.6 | 2.77 | 41.0 | 3.25 | significant |
| | 10 | 62.9 | 3.24 | 54.0 | 3.06 | significant |
| | non treated control: $\bar{x} = 61.2 \pm 3.11$ | | | | | |

FIG. 1 illustrates a graphical presentation of the enhanced fungistatic effect on E. floccosum due to perdeuteriated n-hendecanoic acid and the unlabelled analogue in concentrations as follows: a. 10 μg/ml, b. 25 μg/ml c. 50 μg/ml.

Less sensitive, T. rubrum shows for 50 μg/ml of the perdeuteriated n-hendecanoic acid an inhibition of about 70 percent, compared to about 30 percent of the unlabelled analogue, for 25 μg/ml the inhibition was about 20 percent for the predetermined n-hendecanoic acid compared to no inhibition for the unlabelled analogue (Tab. 5–6, FIG. 4).

Table 5 relates to T. rubrum grown on artificial liquid substrate with or without (non-treated control) addition of perdeuteriated n-hendecanoic acid and the unlabelled analogue. The values reported are mycelial yields (mg/dry weight) after one month period of growth. These represent arithmetical means and standard deviations of seven separate determinations.

TABLE 5

| concentration (μg/ml) | fatty acids C$_{11}$ x̄ | SD | DC$_{11}$ x̄ | SD | t-test |
|---|---|---|---|---|---|
| 100 | 0 | 0 | 0 | 0 | |
| 50 | 37 | 3.21 | 19 | 3.90 | significant |
| 25 | 63 | 10.91 | 52 | 7.98 | indicative |
| 10 | 59 | 8.58 | 64 | 11.30 | not significant |
| 5 | 62 | 9.78 | 60 | 9.54 | not significant |
| 1 | 65 | 11.10 | 63 | 10.61 | not significant |
| non treated control: x̄ = 61 ± 9.64 | | | | | |

Table 6 relates to *T. rubrum* grown on solid substrate (Sabouraud dextrose agar, Difco) with or without (non-treated control) addition of perdeuteriated n-hendecanoic acid and the unlabelled analogue. The reported values are diameters (mm) of fungal colonies. These represent arithmetical means and standard deviations of fifteen separate determinations.

TABLE 6

| age (days) | concentration (μg/ml) | C$_{11}$ x̄ | SD | DC$_{11}$ x̄ | SD | t-test |
|---|---|---|---|---|---|---|
| 5 | 100 | 0 | 0 | 0 | 0 | |
|   | 50 | 10.6 | 2.54 | 4.8 | 1.87 | significant |
|   | 25 | 13.0 | 2.00 | 9.6 | 2.34 | significant |
|   | 10 | 15.2 | 1.63 | 14.7 | 1.41 | not significant |
| non treated control: x̄ = 14.9 ± 1.83 | | | | | | |
| 7 | 100 | 0 | 0 | 0 | 0 | |
|   | 50 | 15.0 | 2.55 | 7.2 | 1.72 | significant |
|   | 25 | 18.6 | 2.07 | 16.2 | 1.64 | significant |
|   | 10 | 22.6 | 1.27 | 21.9 | 1.25 | not significant |
| non treated control: x̄ = 21.9 ± 1.69 | | | | | | |
| 9 | 100 | 0 | 0 | 0 | 0 | |
|   | 50 | 22.2 | 1.19 | 11.0 | 1.01 | significant |
|   | 25 | 26.4 | 1.70 | 22.5 | 1.67 | significant |
|   | 10 | 29.0 | 1.38 | 29.0 | 1.14 | not significant |
| non treated control: x̄ = 31.0 ± 1.66 | | | | | | |
| 11 | 100 | 0 | 0 | 0 | 0 | |
|   | 50 | 27.3 | 1.41 | 12.3 | 1.44 | significant |
|   | 25 | 34.0 | 2.16 | 28.2 | 2.07 | significant |
|   | 10 | 38.7 | 1.90 | 39.9 | 2.23 | not significant |
| non treated control: x̄ = 40.5 ± 2.58 | | | | | | |
| 13 | 100 | 0 | 0 | 0 | 0 | |
|   | 50 | 34.1 | 1.62 | 16.8 | 1.69 | significant |
|   | 25 | 41.5 | 1.58 | 32.7 | 1.99 | significant |
|   | 10 | 49.1 | 2.17 | 48.4 | 1.80 | not significant |
| non treated control: x = 48.1 + 2.16 | | | | | | |
| 15 | 100 | 0 | 0 | 0 | 0 | |
|   | 50 | 40.8 | 2.10 | 22.0 | 2.33 | significant |
|   | 25 | 48.1 | 1.34 | 39.5 | 1.29 | significant |
|   | 10 | 55.2 | 3.11 | 56.1 | 2.61 | not significant |
| non treated control: x̄ = 56.3 ± 2.89 | | | | | | |
| 17 | 100 | 0 | 0 | 0 | 0 | |
|   | 50 | 47.3 | 1.16 | 23.7 | 0.93 | significant |
|   | 25 | 52.0 | 1.27 | 41.6 | 1.90 | significant |
|   | 10 | 64.5 | 2.40 | 62.9 | 2.08 | indicative |
| non treated control: x̄ = 63.2 ± 2.06 | | | | | | |

FIG. 4 illustrates a graphical presentation of the enhanced fungistatic effect on *T. rubrum* due to perdeuteriated n-hendecanoic acid and the unlabelled analogue in concentrations as follows: b. 25 μg/ml, c. 50 μg/ml.

Figure 2:
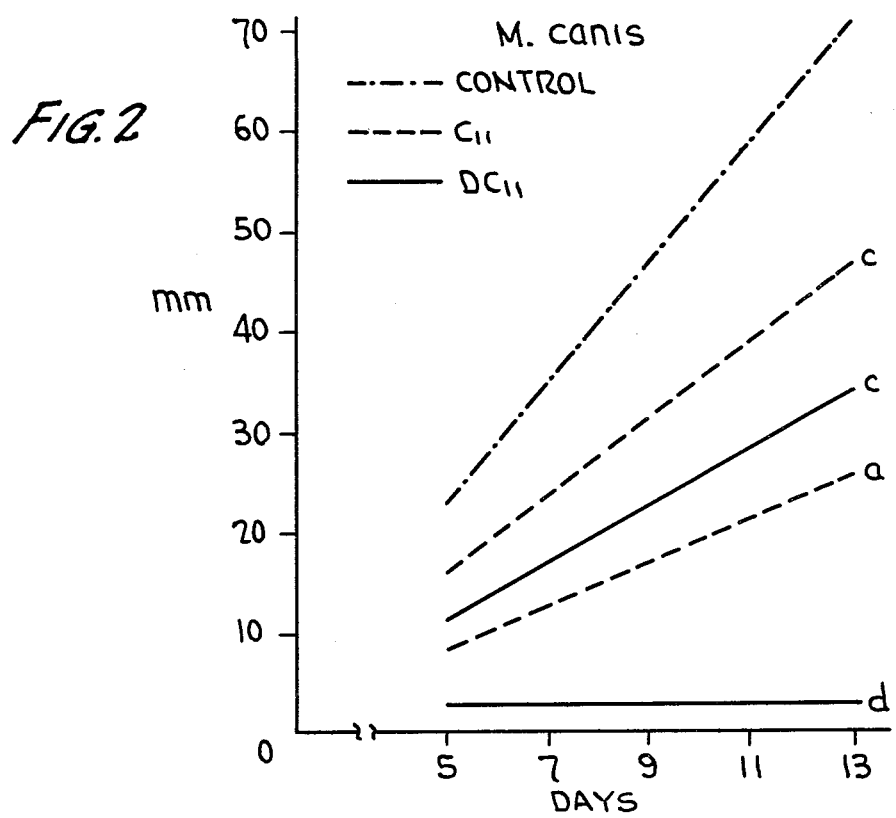

*M. canis* demonstrates a complete inhibition first at 100 μg/ml when exposed to perdeuteriated n-hendecanoic acid and about 70 percent inhibition due to unlabelled analogue; exposure to 50 μg/ml resulted in an inhibition of about 50 percent for the perdeuteriated n-hendecanoic acid compared to about 30 percent for the unlabelled analogue (Tab. 7-8, FIG. 2).

Table 7 relates to *M. canis* grown on artificial liquid substrate with or without (non-treated control) addition of perdeuteriated n-hendecanoic acid and the unlabelled analogue. The values reported are mycelial yields (mg/dry weight) after one month period of growth.

These represent arithmetical means and standard deviations of seven separate determinations.

TABLE 7

| concentration (μg/ml) | C$_{11}$ x̄ | SD | DC$_{11}$ x̄ | SD | t-test |
|---|---|---|---|---|---|
| 100 | 26 | 5.21 | 0 | 0 | significant |
| 50 | 62 | 9.47 | 49 | 6.62 | significant |
| 25 | 90 | 16.64 | 88 | 16.49 | not significant |
| 10 | 86 | 16.34 | 79 | 12.30 | not significant |
| 5 | 94 | 16.81 | 82 | 15.13 | not significant |
| 1 | 87 | 16.27 | 91 | 14.31 | not significant |
| non treated control: x̄ = 87 ± 16.08 | | | | | |

Table 8 relates to *M. canis* grown on solid substrate (Sabouraud dextrose agar, Difco) with or without (non-treated control) addition of perdeuteriated n-hendecanoic acid and the unlabelled analogue. The values reported are diameters (mm) of fungal colonies. These represent arithmetical means and standard deviations of fifteen separate determinations.

TABLE 8

| age (days) | concentration (μg/ml) | C$_{11}$ x̄ | SD | DC$_{11}$ x̄ | SD | t-test |
|---|---|---|---|---|---|---|
| 5 | 100 | 8.0 | 1.19 | 0 | 0 | significant |
|   | 50 | 15.7 | 2.32 | 11.3 | 1.84 | significant |
|   | 25 | 22.3 | 0.96 | 22.7 | 1.25 | not significant |
| non treated control: x̄ = 22.9 ± 0.89 | | | | | | |
| 7 | 100 | 12.4 | 1.52 | 0 | 0 | significant |
|   | 50 | 22.8 | 1.03 | 15.6 | 1.20 | significant |
|   | 25 | 33.0 | 2.27 | 32.2 | 1.95 | not significant |
| non treated control: x̄ = 31.9 ± 2.54 | | | | | | |
| 9 | 100 | 14.8 | 1.36 | 0 | 0 | significant |
|   | 50 | 31.0 | 2.44 | 23.9 | 158 | significant |
|   | 25 | 43.6 | 1.82 | 44.1 | 2.30 | not significant |
| non treated control: x̄ = 46.4 ± 1.40 | | | | | | |
| 11 | 100 | 20.0 | 1.41 | 0 | 0 | significant |
|   | 50 | 38.6 | 2.15 | 29.1 | 2.19 | significant |
|   | 25 | 64.2 | 2.73 | 62.4 | 3.01 | indicative |
| non treated control: x̄ = 61.0 ± 2.62 | | | | | | |
| 13 | 100 | 27.1 | 2.90 | 0 | 0 | significant |
|   | 50 | 46.7 | 3.07 | 33.0 | 2.88 | significant |
|   | 25 | 73.5 | 3.11 | 74.8 | 3.27 | not significant |
| non treated control: x̄ = 71.3 ± 3.41 | | | | | | |

FIG. 2 illustrates a graphical presentation of the enhanced fungistatic effect on *M. canis* due to perdeuteriated n-hendecanoic acid and the unlabelled analogue in concentration as follows: c. 50 μg/ml, d. 100 μg/ml.

Only a slight enhanced antifungal effect due to the perdeuteriation of n-hendecanoic acid was observed on *T. mentagrophytes*. This represents for 100 μg/ml approx. 80 percent inhibition compared to about 70 percent for the unlabelled analogue. When exposed to 50 μg/ml the differences in inhibition between the perdeuteriated n-hendecanoic acid and the unlabelled analogue were only indicative i.e. about 10 percent (Tab. 9-10, FIG. 3).

Table 9 relates to *T. mentagrophytes* grown on artificial liquid substrate with or without (non-treated control) addition of perdeuteriated n-hendecanoic acid and the unlabelled analogue. The values reported are mycelial yields (mg/dry weight) after one month period of growth. These represent arithmetical means and standard deviations of seven separate determinations.

TABLE 9

| concentration | fatty acids | | | | |
|---|---|---|---|---|---|
| | $C_{11}$ | | $DC_{11}$ | | |
| (μg/ml) | $\bar{x}$ | SD | $\bar{x}$ | SD | t-test |
| 100 | 49 | 5.31 | 31 | 2.91 | significant |
| 50 | 122 | 18.55 | 110 | 14.03 | not significant |
| 25 | 129 | 13.40 | 134 | 18.80 | not significant |
| 10 | 141 | 20.77 | 139 | 17.03 | not significant |
| 5 | 137 | 19.86 | 145 | 19.84 | not significant |
| 1 | 140 | 19.83 | 136 | 18.05 | not significant |
| non treated control: $\bar{x} = 133 \pm 19.20$ | | | | | |

Table 10 relates to *T. mentagrophytes* grown on solid substrate (Sabouraud dextrose agar, Difco) with or without (non treated control) addition of perdeuteriated n-hendecanoic acid and the unlabelled analogue. The values reported are diameters (mm) of fungal colonies. These represent arithmetical means and standard deviations of fifteen separate determinations.

TABLE 10

| age (days) | concentration (μg/ml) | fatty acids | | | | |
|---|---|---|---|---|---|---|
| | | $C_{11}$ | | $DC_{11}$ | | |
| | | $\bar{x}$ | SD | $\bar{x}$ | SD | t-test |
| 5 | 100 | 9.0 | 0.83 | 5.2 | 0.92 | significant |
| | 50 | 26.1 | 2.08 | 25.6 | 1.20 | not significant |
| | 25 | 29.6 | 1.44 | 30.1 | 1.37 | not significant |
| non treated control: $\bar{x} = 29.4 \pm 1.61$ | | | | | | |
| 7 | 100 | 15.1 | 1.81 | 7.3 | 1.70 | significant |
| | 50 | 37.5 | 2.18 | 36.8 | 2.35 | not significant |
| | 25 | 43.9 | 2.67 | 43.0 | 2.42 | not significant |
| non treated control: $\bar{x} = 44.3 \pm 2.99$ | | | | | | |
| 9 | 100 | 19.4 | 2.29 | 13.5 | 2.51 | significant |
| | 50 | 52.6 | 2.30 | 51.1 | 2.11 | indicative |
| | 25 | 61.5 | 3.02 | 62.9 | 2.92 | not significant |
| non treated control: $\bar{x} = 62.7 \pm 3.17$ | | | | | | |
| 11 | 100 | 27.0 | 3.26 | 17.8 | 3.50 | significant |
| | 50 | 61.9 | 3.71 | 59.1 | 4.47 | indicative |
| | 25 | 70.7 | 3.90 | 71.0 | 4.22 | not significant |
| non treated control: $\bar{x} = 72.4 \pm 4.82$ | | | | | | |

FIG. 3 illustrates a graphical presentation of the enhanced fungistatic effect on *T. mentagrophytes* due to perdeuteriated n-hendecanoic acid and the unlabelled analogue in concentration as follows: c. 50 μg/ml, d. 100 μg/ml.

Compared to the non treated controls the effect of the perdeuteriated n-hendecanoic acid was generally statistically significant for concentrations over 10 μg/ml.

The respiratory measurements in short time experiment show that deuteriation of the fatty acids does not exercise an immediate enhanced antifungal effect. The only exception was *E. fluoccosum*.

FIG. 5 illustrates the oxygen consumption of *E. floccosum*, when exposed to perdeuteriated n-hendecanoic acid (b. 25 μg/ml, c. 50 μg/ml) expressed as a percentage of the unlabelled analogue. The values represent arithmetical means and standard deviations of seven separate determinations.

The present results show that perdeuteriation of fatty acids leads to an increase in their antifungal activity on dermatophytes in vitro conditions. This enhanced effect is dependent upon both chain length and the species tested. Perdeuteriation of n-hendecanoic acid increases statistically significantly its effect on all dermatophyte tested. The ranking of sensitivity from the most sensitive to the least sensitive was: *E. floccosum*, *T. rubrum*, *M. canis* and *T. mentagrophytes*. The increased antimycotic effect on dermatophytes was always correlated to an increased concentration of the fatty acids.

A most likely interpretation of the unlabelled fatty acids effect is that the growth inhibition probably appears when the intracellular concentration rises above a certain level indicating the presence of a barrier to the absorption of the acid. This barrier becomes increasingly important as the chain length increases, which points to the fact that the growth limitation of these substances is due, at least in part, to their poor solubility in the aqueous media. As the undissociated molecules of acids penetrate the cell membrane more readily than the corresponding ions, the effect appears to be due essentially to the concentration of the undissociated acid. This is in agreement with earlier observations on the antifungal action of carboxylic acids, which also showed that growth inhibition is a function of the concentration of undissociated acid over a wide pH range. Thus, the growth inhibition is observed when the intracellular concentration rises above a certain level. This concentration is once again determined by the external concentration of undissociated acid. Perdeuteriation significantly increases the molecular dissociation, which may result in the enhanced effect, especially of the n-hendecanoic acid.

Furthermore, it has been postulated that the inhibitory effects of the unlabelled fatty acids probably are due to absorption of the fatty acids onto enzymatic sites in the fungal cells. When the concentration of external fatty acids reaches a sufficiently high level to permanently cover all enzymatic sites, all fungal activity ceases. The perdeuteriated fatty acids have larger molecules, so that blockage of the enzymatic system may be more effective.

Moreover, carbon-deuterium bonds are more stable than carbon-protium bonds—the zero energy of the carbon-deuterium bond is usually 1.2 to 1.5 kcal/mol less than that of the carbon-protium bond—thus the increased stability of the molecule may play a role such that the fungus may not be so readily able to eliminate the fungistatic agent.

In order to visualise the morphological changes of *Epidermophyton floccosum* associated with exposure to perdeuteriated n-hendecanoic acid, the architecture of the dermatophyte was investigated by means of interference contrast and scanning electron microscopy. The morphology of mycelia grown on substrate containing perdeuteriated n-hendecanoic acid, or the unlabelled analogue, was compared. The perdeuteriated n-hendecanoic acid produced a characteristic undulant effect of the hyphae. The characteristic wave-like appearance of the mycelia looked similar to the curling effect occuring after treatment of dermatophytes with griseofulvin, but was not as pronounced. Perdeuteriated n-hendecanoic acid, unlike the unlabelled analogue, also seems to cause a reduction of the number of chlamydospores and perforations of the macroconidia.

The changes in the morphological structure of *Epidermophyton floccosum* exposed to perdeuteriated n-hendecanoic acid have been investigated. Morphological examination of mycelia exposed to this substance by interference contrast microscopy demonstrated a picture of defect hyphae and macroconidia. By the aid of scanning electron microscopy we have attempted to obtain a better visualization of these changes at ultrastructural level.

A small mycelia fragment from monosporically selected strains of *Epidermophyton floccosum* was incubated in humide Petri dishes for five days at 30° C. on circular cover glasses ($\phi$ 10 mm). Two series of 20 glasses each were coated with a thin layer of Sabouraud dextrose agar (Difco) with additions of 10 $\mu$g/ml of perdeuteriated n-hendecanoic acid, or its unlabelled analogue. The fatty acids were dispersed in the still warm substrate by an Ultra-Turrax (IKA) homogenisator, before the application.

A Zeiss microscope with interference contrast optics was used to demonstrate possible morphological changes in wet and unstained samples. Smears of the mycelium were examined in saline solution or in a medium containing equal amounts (w/w) of lactic acid, crystallized phenol, glycerol and distilled water. Samples grown on cover glasses were examined in air.

Samples grown on cover glasses, as previously described, were transferred to 70% ethanol or to 3% glutaraldehyde in 0.1M phosphate buffer, pH 7.2, and kept there overnight. Samples fixed in glutaraldehyde were then brought to 70% ethanol for 30 min. From this point all samples were dehydrated through a graded ethanol series (85%: 30 min, 90%: 30 min, 100%: 2×30 min). Then they were transferred to cellosolve (2-ethoxyethanol) which was used in place of amyl acetate before drying with liquid carbon dioxide by the critical point method.

The dry specimens were coated with silver and gold (1:3) on a rotating stage to a thickness approximately corresponding to 250 A, if the specimen surface had been flat to the direction of evaporation. The specimens were examined in a Cambridge Stereoscan S-4 at 5 kV.

The differences between the groups compared were tested using the Signtest of three randomly selected view fields in each of the 20 samples from the two groups. Level of significance 95%, double sided interval.

When examined by means of the method the interference contrast microscopy mycelia of *Epidermophyton floccosum* exposed to the perdeuteriated n-hendecanoic acid showed in all 20 samples the following signs of growth retardation: a characteristic undulant effect on the mycelia of the fungus (FIG. 7) the wave-like appearance were, however, not so pronounced as the curling effect seen after exposure to griseofulvin. An indicative reduction of the number of chlasmydospores was also observed. These morphological abnormalities were not found in any of the mycelia exposed to n-hendecanoic acid (FIG. 6). The magnification in FIGS. 6 and 7 is 1000.

By scanning electron microscopy the differences between mycelia exposed to perdeuteriated n-hendecanoic acid and to the unlabelled analogue could be demonstrated with still better significance. The undulant pattern of hyphae was very typical in the medium containing perdeuteriated n-hendecanoic acid, FIG. 9 but not in the controls with the unlabelled analogue, FIG. 8. It was apparent that especially the vegative mycel showed this abnormal pattern, while the air mycel was generally normal. Perforation of hyphal segments was also observed (FIG. 10) probably indicating wall damage caused by the perdeuteriated n-hendecanoic acid.

The mycelium of *Epidermophyton floccosum* exposed to perdeuteriated n-hendecanoic acid reveals in contrast to those exposed to the unlabelled analogue, showed in a statistically significant number of samples characteristic structural changes, which can be demonstrated by the aid of interference contrast microscopy. In the scanning electron microscope, it was possible however, to observe very discrete and early signs of damages of the filaments, not visible in the interference contrast microscope. The most pronounced effect is the undulant waving of the hyphae exposed to perdeuteriated n-hendecanoic acid which was clearly demonstrated in all samples. Generally, however, aerial hyphal filaments did not show this undulant effect. For the undulant effect a direct contact between the mycelium and the nutrient substrate is probably necessary.

By the aid of the scanning electron microscope we also demonstrated perforations of the macroconidia in a statistically significant number of the samples exposed to perdeuteriated n-hendecanoic acid, but not in the controls. Such perforations are normally not found in this dermatophyte. Of course such more or less irregular "holes" and areas with sharply marked edges may be artifacts, i.e. gas bubbles in the embedding media, but the fact that they are not found in the control series, may contradict this explanation. The perforations appeared in the apical cell of the mycelia. As the conidial formation of *Epidermophyton floccosum* takes place from a single basal cell, represented by an apical cell of the hyphae, the apical cells are the most important for the fungal growth. Damage of the apical cells is also associated with a reduced dominance of the apical segment. An indicative reduced number of chlamydospores found compared to the preparations exposed to unlabelled n-hendecanoic acid may be a sign of a decreased viability of the fungus.

Our studies on the morphology of *Epidermophyton floccosum* exposed to perdeuteriated n-hendecanoic acid have thus shown changes on the dermatophyte indicating an enhanced antimycotic effect due to deuteriation of the n-hendecanoic acid. The characteristic wave-like appearance of the mycelia looks similar, but is not as pronounced as, the curling effect occuring after treatment of dermatophytes with griseofulvin.

The experiments referred to above indicate a decreasing of fungistasis with an increasing carbon-chain length of the perdeuteriated fatty acids. We have attempted to verify this observation in vivo conditions. A special interest was, of course, focused on the most promising compound, the perdeuteriated n-hendecanoic acid.

Normal chain perdeuteriated fatty acid homologues, synthesized as previously described, as hendecanoic, dodecanoic and tetradecanoic acids, as well as caesium salts of hexadecanoic and octadecanoic acids, were compared with their unlabelled analogues. The fatty acids or their salts were dispersed in the vehicles by the aid of Ultra-Turrax homogeniser (IKA). The test concentrations were 1 and 2%. Vehicles used were: dist. water, propylene glycol and dimethyl-sulphoxide (DMSO, 20%). A known antimycotic substance, gentian violet (0.5%) in dist. water was used as an internal standard. Hydrocortisone phosphate (1%) was also added in some of the trial series with the intention to enhance the growth of dermatophytes.

Monosporically selected strains of *Microsporum canis* Bodin (1902), originating from our collection, were prepared as dense mycelial suspensions in water.

Albino Guinea pigs with an average weight of 300 g were used. None of the Guinea pigs had any mycotic infection before the investigation started. The number of Guinea pigs in the test series varied between 2 and 48.

The following methods based on the ability of *Microsporum canis* to cause alopecia in Guinea pigs were used for evaluation of the antimycotic properties of the test substances.

Method 1. Each Guinea pig was infected with a mycelial suspension on the right and the left side in three areas of 3 mm diameter. The areas were 2.5 cm apart. Infecting was performed on three successive days. On the fourth day, when the infections were manifest, the treatment started. The left side was treated from the fourth to the eighth day, twice daily with the trial substance on one side and a placebo on the other. Four weeks after the infecting procedure the area of alopecia around the points of infection was measured.

Method 2. Similar to method 1. Thus at three points, 3 mm in diameter and 2.5 cm apart on the right and left side of the Guinea pig, a mycelial suspension was applied on circular filter paper, 5 mm in diameter as a conventional patch test unit. Around the filter paper was placed an inert circular thin paper, 2 cm in diameter. Occlusive bandage was applied.

The procedure was performed twice during three successive days. On the fourth day the application of the substances began. The solutions were put on a filter paper disc in the same unit as was used for infecting. An occlusive elastic bandage encircling the trunk was applied.

Method 3. The Guinea pigs were shaved on a square area, 3×3 cm. The surface was then gently sandpapered with a finegrained sandpaper on each side. The mycelial suspensions were applied on the two fields. The infection reached its maximum after three days. From the fourth to the eighth day and from the eleventh to the fifteenth day after the infecting, one side was treated with the deuteriated fatty acid and the other with a placebo substance. Four weeks after the infecting procedure the growth rate in the areas of alopecia within a squared field was measured and the intensity of the inflammation, crusting and eventual eczema judged.

Method 4. Similar to method 3, i.e. shaved square surfaces, 3×3 cm, were infected by applying filter papers of the size 3×3 cm and containing the mycelial suspension. Occlusive bandage was applied. The infecting procedure was repeated twice during the three following days.

The test substances were added to filter paper pieces, 3×3 cm, and applied on a shaved area. An occlusive elastic bandage was applied to keep the paper pieces in situ.

Transparent cellulose film was used to transfer the size of the areas caused by the growing fungus. The areas were then cut out and the weight of the pieces was determined. The surface of the infected areas was calculated by comparison with the weight of the cellulose film (1 $cm^2$).

The differences in size of the areas of alopecia was statistically tested using the Student's t-test, 95 percent double sided interval. The measurement error was determined by measuring fifteen pieces of cellulose paper, weighing them and comparing the resulting areas with planimetrically achieved results. The measurement error was negligible and does not affect the paired comparisons.

The results are summarized in Table 11.

TABLE 11

Area of alopecia caused by *Microsporum canis* in experimental microsporic in Guinea pigs after application of perdeuteriated hendecanoic acid and non-deuteriated analogue.

| Perdeuteriated fatty acid (PDFA) | Placebo | Method (no.) | Conc. (%) of FA | Vehicle for FA | Animals (no.) | Areas | Alopecia (sq. mm) | | | | Student's t-test |
|---|---|---|---|---|---|---|---|---|---|---|---|
| | | | | | | | PDFA | | Placebo | | |
| | | | | | | | $\bar{x}$ | SD | $\bar{x}$ | SD | |
| Perdeuteriated hendecanoic acid | Hendecanoic acid | 1 | 1 | Spir.dil. | 5 | 15 + 15 | 85.7 | 31.7 | 256.0 | 112.0 | Significant |
| Perdeuteriated hendecanoic acid | Hendecanoic acid | 1 | 1 | propyl.gl. | 48 | 144 + 144 | 159.9 | 125.1 | 203.2 | 152.4 | " |
| Perdeuteriated hendecanoic acid | Gentians violet 0.5% | 1 | 2 | " | 27 | 81 + 81 | 133.3 | 76.3 | 204.8 | 100.9 | " |
| Perdeuteriated hendecanoic acid | Hendecanoic acid | 3 | 2 | Spir.dil. | 9 | 9 + 9 | 42.2 | 20.4 | 264.0 | 67.2 | " |
| Perdeuteriated hendecanoic acid | DMSO 20% | 2 | 1 | " | 5 | 10 + 5 | 24.5 | 17.5 | 105.0 | 64.2 | " |
| Perdeuteriated hendecanoic acid | Hendecanoic acid | 4 | 1 | DMSO 20% | 3 | 3 + 3 | 633.0 | 57.7 | 833.0 | 89.2 | " |
| Perdeuteriated hendecanoic acid | Hendecanoic acid | 4 | 1 | Propyl.gl. | 2 | 2 + 2 | 350.0 | 50.0 | 650.0 | 50.0 | " |
| Perdeuteriated hendecanoic acid + Hydrocortisone phosphate 1% | Hendecanoic acid + Hydrocortisone phosphate 1% | 4 | 1 | " | 6 | 6 + 6 | 391.7 | 46.0 | 458.0 | 54.0 | " |

The perdeuteriated n-hendecanoic acid had a statistically significant better antimycotic effect than the unlabelled analogue. This was demonstrated for a concentration of 1% of perdeuteriated n-hendecanoic acid and its unlabelled analogue using methods 1, 2, 4 and for a concentration of 2% using method 3.

Using method 1 it was also demonstrated that 2% perdeuteriated n-hendecanoic acid was significantly more effective than 0.5% gentian violet.

When the dimethyl sulphoxide (DMSO) was added to increase the penetration of perdeuteriated n-hendecanoic acid and its unlabelled analogue in a concentration of 1% it could be demonstrated (method 2) that perdeuteriated n-hendecanoic acid was still superior to its unlabelled analogue. The occlusive technique, however, gave rise to a central necrosis in the DMSO treated areas. The perdeuteriated n-hendecanoic acid (1%) was significantly more effective than 20% DMSO (method 2).

Perdeuteriated n-hendecanoic acid (1%) combined with 1% hydrocortisone phosphate (1%) also had a significantly higher effect than the unlabelled analogue combined with hydrocortisone phosphate using method 4.

Within the series the matched paired results are comparable. However, it is not possible to make any exact comparisons between the different series due to rather large biological variations between the animals.

Comparisons were also made between perdeuteriated fatty acids homologues ($C_{12}$–$C_{18}$) and their unlabelled analogues but no significant differences were found in any of these series in 1–2% concentrations (method 1).

From the present results it is evident that the perdeuteriated n-hendecanoic acid has a greater antifungal effect on experimental microsporic in Guinea pigs compared to its ullabelled analogue.

This was demonstrated by four different in vivo methods used. This is in accordance with our in vitro observations.

In moderate doses hydrocortisone phosphate stimulates the growth of dermatophytes. Therefore, it was added to perdeuteriated n-hendecanoic acid and its unlabelled analogue in one of the test series. Even then perdeuteriated n-hendecanoic acid was superior to its unlabelled analogue.

Dimethyl sulphoxide (DMSO) has been shown to increase the penetration of substances through the skin, probably by increasing the passive flow between the cells and giving rise to a swelling of the *stratum corneum*, which makes the layer more porous. DMSO in 20% concentration was used in one of the test series in addition to perdeuteriated n-hendecanoic acid and its unlabelled analogue. The perdeuteriated n-hendecanoic acid in DMSO was found to be significantly more effective than the unlabelled analogue in DMSO. Perdeuteriated n-hendecanoic acid also had a significantly better effect than DMSO itself. The latter gave rise to the skin necrosis in many Guinea pigs (the methods with encircling occlusive bandage).

The studies performed on $C_{12}$–$C_{18}$ fatty acids, comparing their perdeuteriated and unlabelled analogues, show that they do not give rise to statistically significant differences in antifungal effect due to the perdeuteriation. The vehicles spir.dil. and propylene glycol had no antimycotic effect in control (3 animals) trials (method 1). The effect of fatty acids towards dermatophytes decreases with increasing carbon chain. Thus differences in the effect of e.g. perdeuteriated n-hendecanoic acid and perdeuteriated caesium n-octadecanoate might be due to differences in their chain length.

The *stratum corneum* is protected against physical, chemical and microbial assaults by a film of fine dispersed lipids. Therefore as prerequisite, parasitic dermatophytes must include an ability of the fungus to split the environmental fats and utilized the hydrolysis products as a prime energy and carbon source. The skin surface lipids together with some water soluble constituents of *stratum corneum*, therefore represent a favourable substrate for growing spores. This is of importance, especially in the early stage of the disease, namely before the fungus has established permanent contact with keratin. As the perdeuteriated fatty acids are rather similar to the fatty acids naturally occuring to the skin surface, the enzymatic system of dermatophytes also metabolize them in vivo conditions.

If a substance is expected to have antimycotic properties in vivo, it must have the ability to penetrate *stratum corneum*. The penetration of some fatty acids through the skin has been investigated. Generally the penetration decreases with increasing carbon chain length.

The antimycotic active substance, after penetration of *stratum corneum*, must reach and penetrate the fungal cells. As the middle-chain fatty acids are more soluble in the aqueous phase than the long-chain ones, the penetration of the middle-chain fatty acids is superior to their higher homologues. Our in vitro investigations indicate that perdeuteriated n-hendecanoic acid reaches the fungal cells in concentrations high enough for a complete growth inhibition.

The present investigations have thus shown that perdeuteriated n-hendecanoic acid gives rise to an enhanced antifungal activity on dermatophytes under in vivo conditions compared to its unlabelled analogue. Deuterium effects in biological systems are extremely complex and a combination of several effects may be involved. The toxicity of deuteriated substances is comparatively low, vide Katz, J. J. & H. L. Crespi (1970) Isotope effects in biological systems. In C. J. Collins & N. S. Bowman, Isotope effects in chemical reactions, chap. 5. Van Nostrand Reinhold Co., New York-Cincinnati-Toronto-Melbourne.

On patients with onychomycosis, caused by typical dermatophyte (*Trichophyton mentagrophytes*) verified by culture, 1% n-hendecanoic acid, perdeuteriated resp. non-deuteriated was applied in a vehicle of 70 percent ethanol for 3 weeks. One nail was treated with perdeuteriated n-hendecanoic acid and the other nail with the non-deuteriated analogue on the same patient. The treatment period was about 3 weeks and the dosage (application rate) 3 times a day. All nails investigated were totally destroyed by the fungus. After 4 months the nails treated with perdeuteriated n-hendecanoic acid showed a healthy nail plate from the matrix and about 8 mm in distal direction. The most distal parts of the nails still were affected by the fungus. No healing was observed after treatment with non-perdeuteriated n-hendecanoic acid. The trial demonstrated that perdeuteriated n-hendecanoic acid apparently has a potentiated antimycotic effect on the nail infected. After 3 weeks of treatment a healthy nailplate grows out from the matrix. The distal damaged nail successively grows in distal direction and is removed.

The tolerability of deuteriated n-hendecanoic acid was considered to be excellent and no side effects were observed.

What is claimed is:

1. A method of inhibiting fungi growth on a biological object comprising contacting the fungi with a composition comprising a vehicle and an amount effective to inhibit fungi growth of perdeuteriated N-hendecanoic acid or 2,2-dideutero-N-hendecanoic acid.

* * * * *